United States Patent [19]

Muller

[11] Patent Number: 4,709,697

[45] Date of Patent: Dec. 1, 1987

[54] TISSUE PNEUMATIC SEPARATOR STRUCTURE AND METHOD

[75] Inventor: George H. Muller, Ann Arbor, Mich.

[73] Assignee: Joseph J. Berke, Detroit, Mich. ; a part interest

[21] Appl. No.: 582,971

[22] Filed: Nov. 21, 1983

Related U.S. Application Data

[63] Continuation of Ser. No. 214,006, Dec. 9, 1980, abandoned, which is a continuation-in-part of Ser. No. 103,206, Dec. 13, 1979, Pat. No. 4,357,940.

[51] Int. Cl.$^4$ ............................................. A61B 17/00
[52] U.S. Cl. ................................................ 128/303 R
[58] Field of Search ..................... 128/304, 305, 305.1, 128/310, 755, 24 A, 20, 303 R; 604/22; 15/405, 316 R; 222/3; 239/DIG. 20, DIG. 21, DIG. 22; 30/123.3

[56] References Cited

U.S. PATENT DOCUMENTS

| | | | |
|---|---|---|---|
| 742,305 | 10/1903 | Garhart | 128/303 R |
| 3,828,771 | 8/1974 | Gartner | 128/62 A |
| 4,019,260 | 4/1977 | Levy et al. | 34/97 |
| 4,106,501 | 8/1978 | Ozbey | 128/62 A |
| 4,294,251 | 10/1981 | Greenwald et al. | 128/240 |
| 4,411,265 | 10/1983 | Eichenlaub | 128/304 X |

FOREIGN PATENT DOCUMENTS 301032 1/1930 United Kingdom ............... 30/123.3

448013 7/1975 U.S.S.R. ............................ 128/305

Primary Examiner—Michael H. Thaler
Attorney, Agent, or Firm—Dale R. Small & Associates

[57] ABSTRACT

Tissue separator structure and method which in its simplest form comprises a mechanical nudger on the end of a stem for mechanically separating tissue and in the preferred embodiment includes a fluid medium passing through the stem and out of a floating tip to separate the tissue with the directed, controlled pressure of the fluid medium and/or nudging by the floating tip. In a more sophisticated embodiment of the invention, plural fluid medium forces are provided on the tissue to be separated to perform separating and clearing operations and in further embodiments, the area of the tissue being separated may be moistened and/or fluid and debris removed from the area of tissue separation. The stem may be disposable in accordance with the invention. Further in accordance with the method of the invention, tissue is separated by mechanical nudging and/or by means of a fluid medium under pressure. The method may include the steps of moistening the tissue to be separated or withdrawing fluid and debris from the area of the tissue to be separated. In one modification of the method of the invention, the structure of the invention may be used to clean the teeth with fluid pressure from a water faucet or the like and/or the water pressure regulated and/or formed in pulses.

31 Claims, 19 Drawing Figures

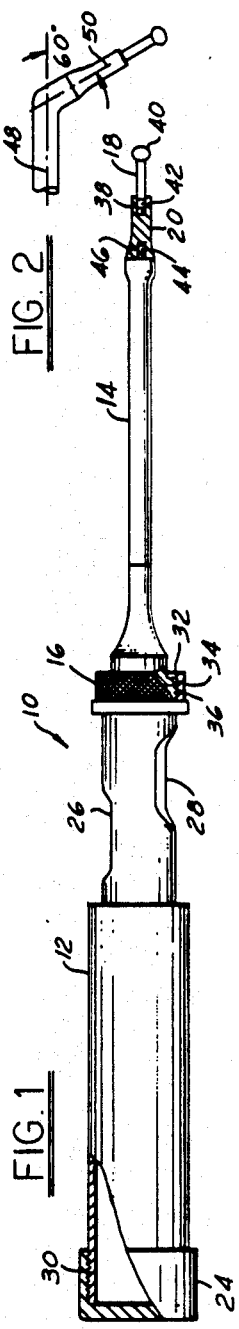
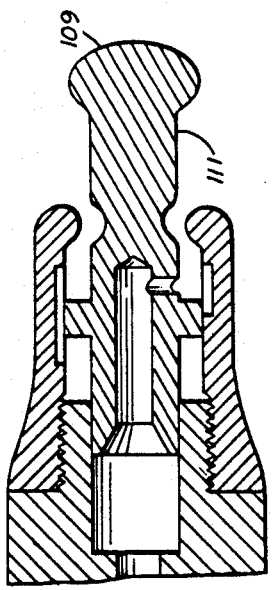
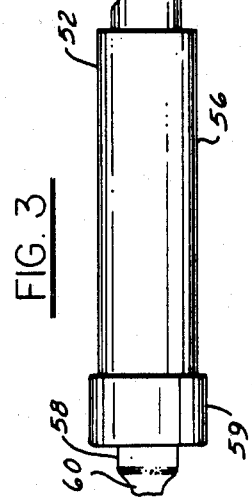
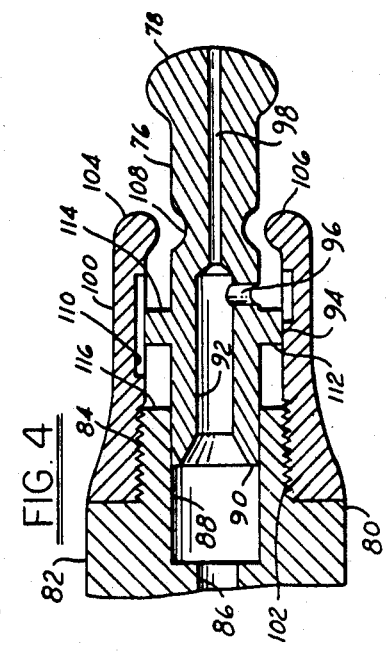

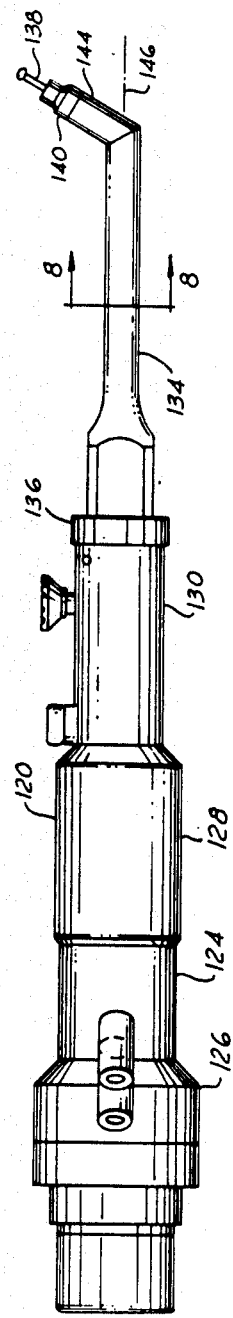
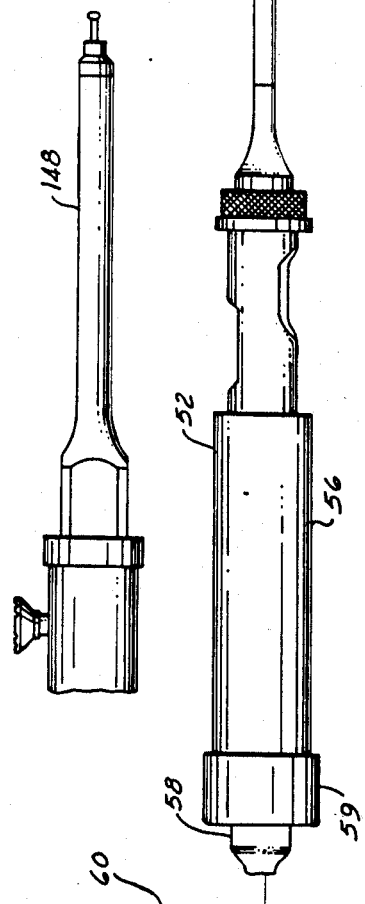
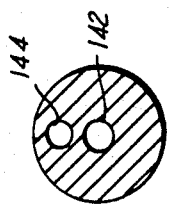
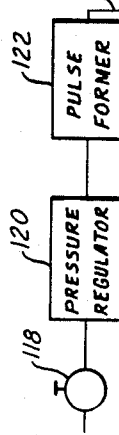

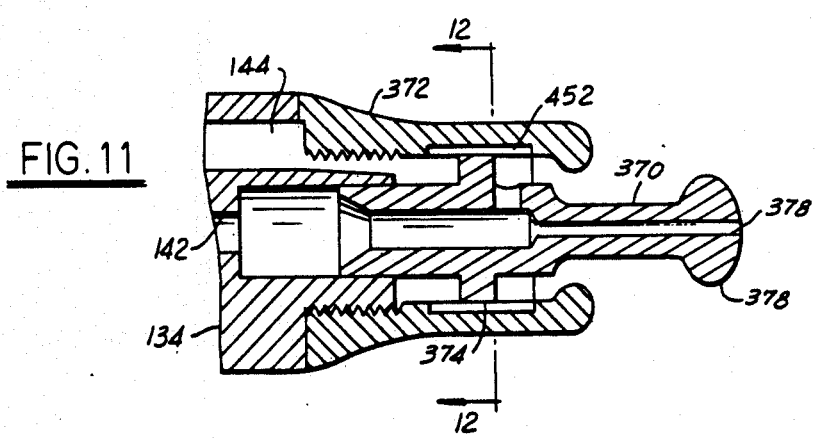
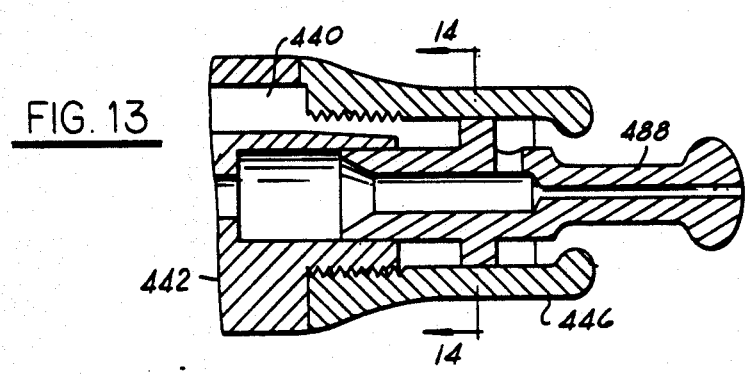
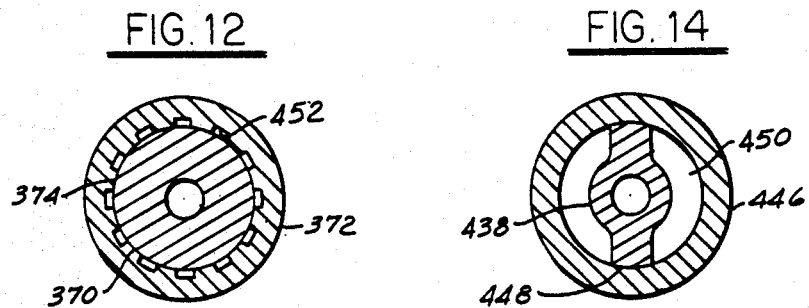

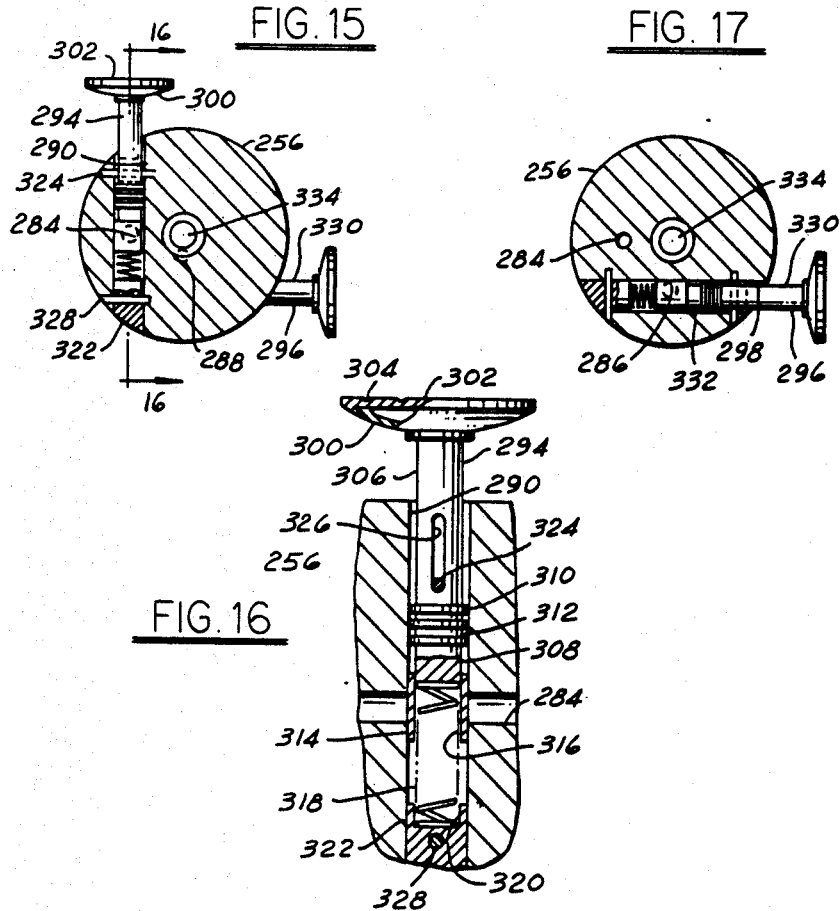

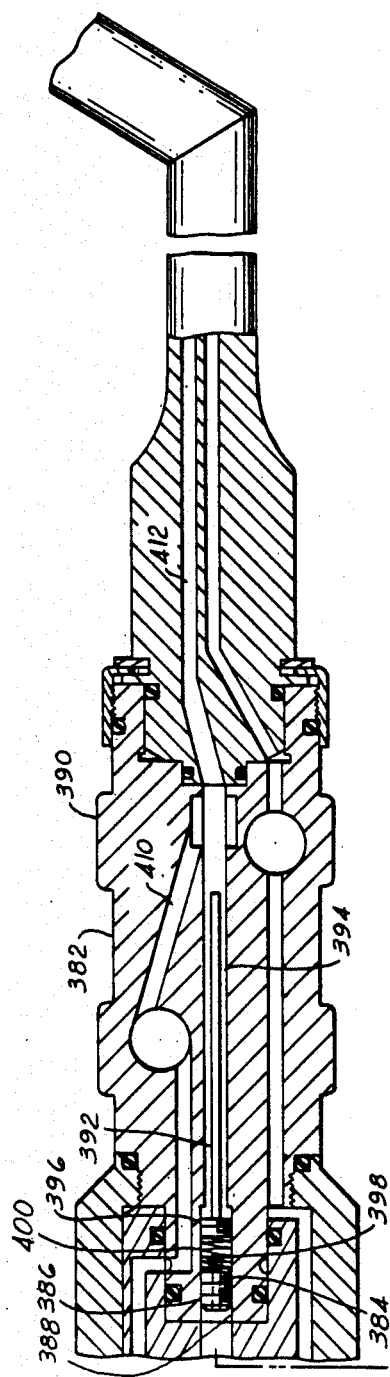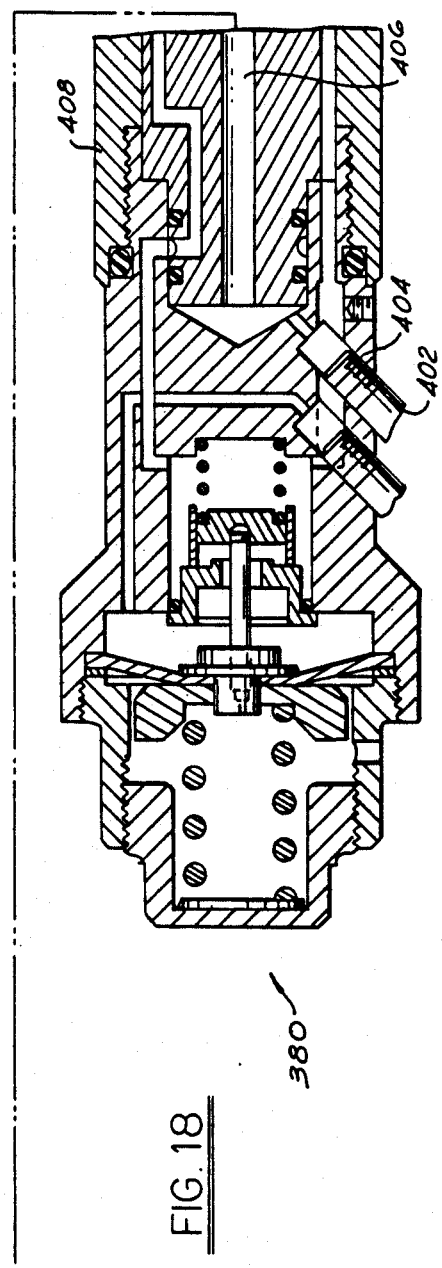
FIG. 18

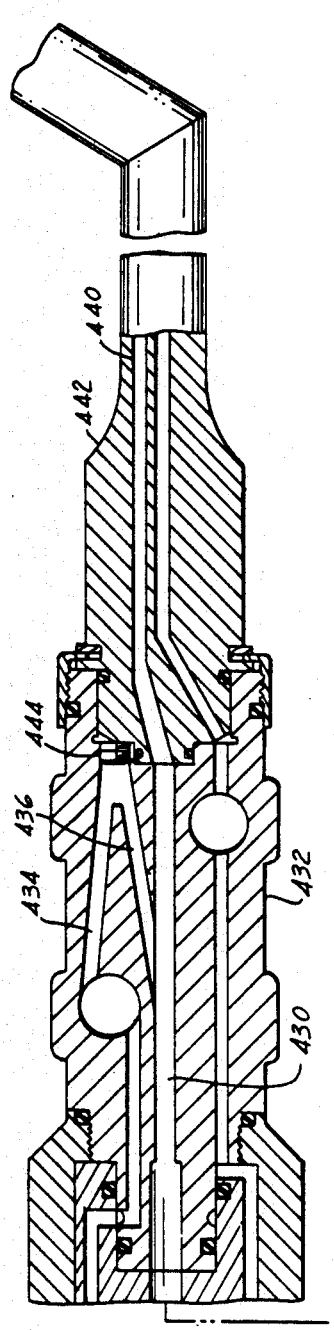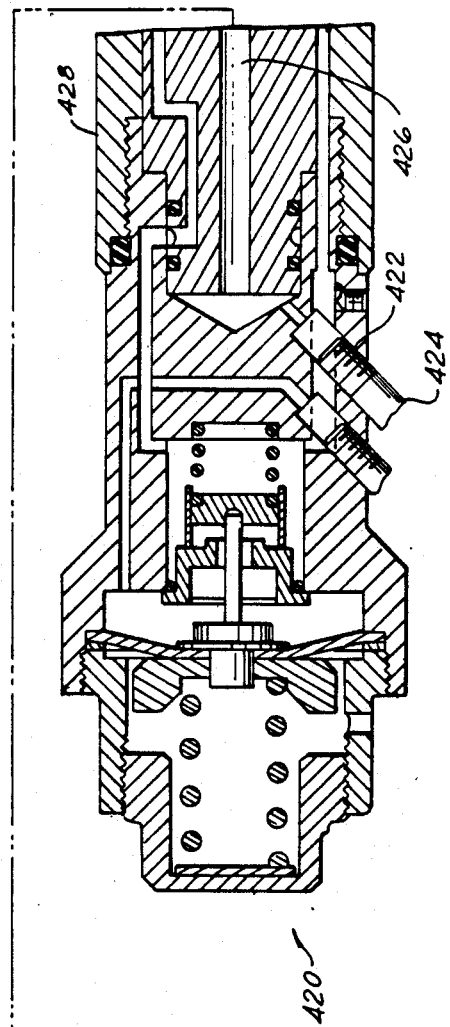
FIG. 19

TISSUE PNEUMATIC SEPARATOR STRUCTURE AND METHOD

This is a continuation of application Ser. No. 214,006 filed Dec. 9, 1980, abandoned which is a continuation-in-part of Ser. No. 103,206, filed Dec. 13, 1979 now U.S. Pat. No. 4,357,940.

BACKGROUND OF THE INVENTION

1. Field of the Invention

The invention relates to tissue separators and refers more specifically to a tissue pneumatic separator for directing a suitable fluid such as nitrogen gas under pressure toward tissue layers to be separated at a controlled pressure through an orifice or jet in a controlled direction, and the method of using such a device to direct a suitable fluid under the controlled pressure and in a controlled direction through an orifice toward tissue to be separated.

2. Description of the Prior Art

In the past, structure for separating tissue such as tumor sacs or membranes from surrounding healthy tissue have primarily been cutting devices and/or high frequency vibrating structures. Cutting devices such as scalpels have sometimes caused undesirable damage to and bleeding from tissue being separated. High frequency vibrating heads often use cumbersome umbilical connections to nearby generators with electrical power inputs and are very expensive. All such prior devices have of necessity required extreme care and delicate manipulation in their use to minimize damage to the tissue being separated.

SUMMARY OF THE INVENTION

In its simplest form, the invention comprises a tissue separator approximately the size of a felt pen having a mechanical nudging tip thereon for physically nudging the tissue to be separated to provide tissue separation. In the preferred embodiment, the invention is a tissue pneumatic separator wherein a suitable gas at a controlled head pressure flows through a calibrated orifice in a floating tip in variously controlled directions to separate layers of tissue rapidly and accurately without damage to the tissue or membranes being separated. The tip of the tissue pneumatic separator of the invention floats on balanced cushions of the gas to limit the nudging pressure applied by the floating tip.

In a sophisticated embodiment of the tissue pneumatic separator, nitrogen gas is variably controlled in pressure and may be passed to the floating tip through at least two separate controls operable either by a surgeon's thumb or his forefinger. In one modification of the tissue pneumatic separator of the invention, gas used in the separation of tissue and flowing forward through the calibrated orifice of the floating tip is controlled by the surgeon's forefinger while moisturizing fluid is passed forward around the floating tip of the tissue pneumatic separator and controlled by the physician's thumb. In another modification of the tissue pneumatic separator, the gas utilized to separate tissue and flowing forward through the calibrated orifice of the floating tip is controlled by the surgeon's forefinger while excess fluids in the area of the tissue being separated may be withdrawn rearward by suction around the floating tip of the tissue pneumatic separator under control of the surgeon's thumb.

In accordance with the method of the invention form, tissue to be separated is physically nudged by a bulbous tip affixed to the tissue separator stem and body assembly. In a preferred embodiment of the invention, tissue is separated by nitrogen gas passing through a floating tip of the tissue pneumatic separator, which tip may also be used to nudge the tissue being separated under a controlled and balanced gas pressure. In further modifications of the method of the invention, moisturizing fluid may be passed to the tissue being separated at the same time the tissue is being separated by gas directed thereon and/or physical nudging, or fluid may be removed from the area of the tissue being separated in accordance with the method of the invention at the same time tissue separation is being accomplished.

BRIEF DESCRIPTION OF THE DRAWINGS

FIG. 1 is a partly broken away, generally elevation view of a tissue separator constructed in accordance with the invention for effecting the method of the invention.

FIG. 2 is a partial elevation view of a modification of the tissue separator illustrated in FIG. 1 showing a tip extending at an angle to the longitudinal axis of the separator.

FIG. 3 is a partly broken away, generally elevation view of a tissue pneumatic separator constructed in accordance with the invention for effecting the method of the invention.

FIG. 4 is an enlarged section view of a floating tip for use with the tissue pneumatic separator of FIG. 3.

FIG. 5 is an enlarged section view similar to that of FIG. 4, showing a modified floating tip.

FIG. 6 is a block diagram of hydraulic structure for use in conjunction with the structure of the invention in a dental application.

FIG. 7 is an elevation view of a more sophisticated embodiment of the tissue pneumatic separator of the invention for practicing the method of the invention.

FIG. 8 is an enlarged cross section of the stem of the tissue pneumatic separator illustrated in FIG. 7, taken substantially on the line 8—8 in FIG. 7.

FIG. 9 is a partial elevation view of a modification of the tissue pneumatic separator illustrated in FIG. 7 showing a straight stem.

FIG. 11 is an enlarged longitudinal section view of the end of the stem, the floating tip, and tip retainer of the tissue pneumatic separator illustrated in FIG. 10.

FIG. 12 is a cross section of the floating tip and tip retainer illustrated in FIG. 11, taken substantially on the line 12—12 in FIG. 11.

FIG. 13 is a longitudinal section view similar to FIG. 11, but showing a modified floating tip and tip retainer.

FIG. 14 is a cross section of the modified floating tip and tip retainer illustrated in FIG. 13, taken substantially on the line 14—14 in FIG. 13.

FIG. 15 is an enlarged cross section of the valve unit of the tissue pneumatic separator of FIG. 10, taken substantially on the line 15—15 in FIG. 10.

FIG. 16 is an enlarged partial cross section of the valve unit of the tissue pneumatic separator of the invention shown in FIG. 10, taken substantially on the line 16—16 in FIG. 15.

FIG. 17 is an enlarged cross section of the valve unit of the tissue pneumatic separator of FIG. 10, taken substantially on the line 17—17 in FIG. 10.

FIG. 18 is a broken longitudinal section of a modification of the tissue pneumatic separator illustrated in FIG. 10.

FIG. 19 is a broken longitudinal section of another modification of the tissue pneumatic separator illustrated in FIG. 10.

DESCRIPTION OF THE PREFERRED EMBODIMENT

Figure 10:
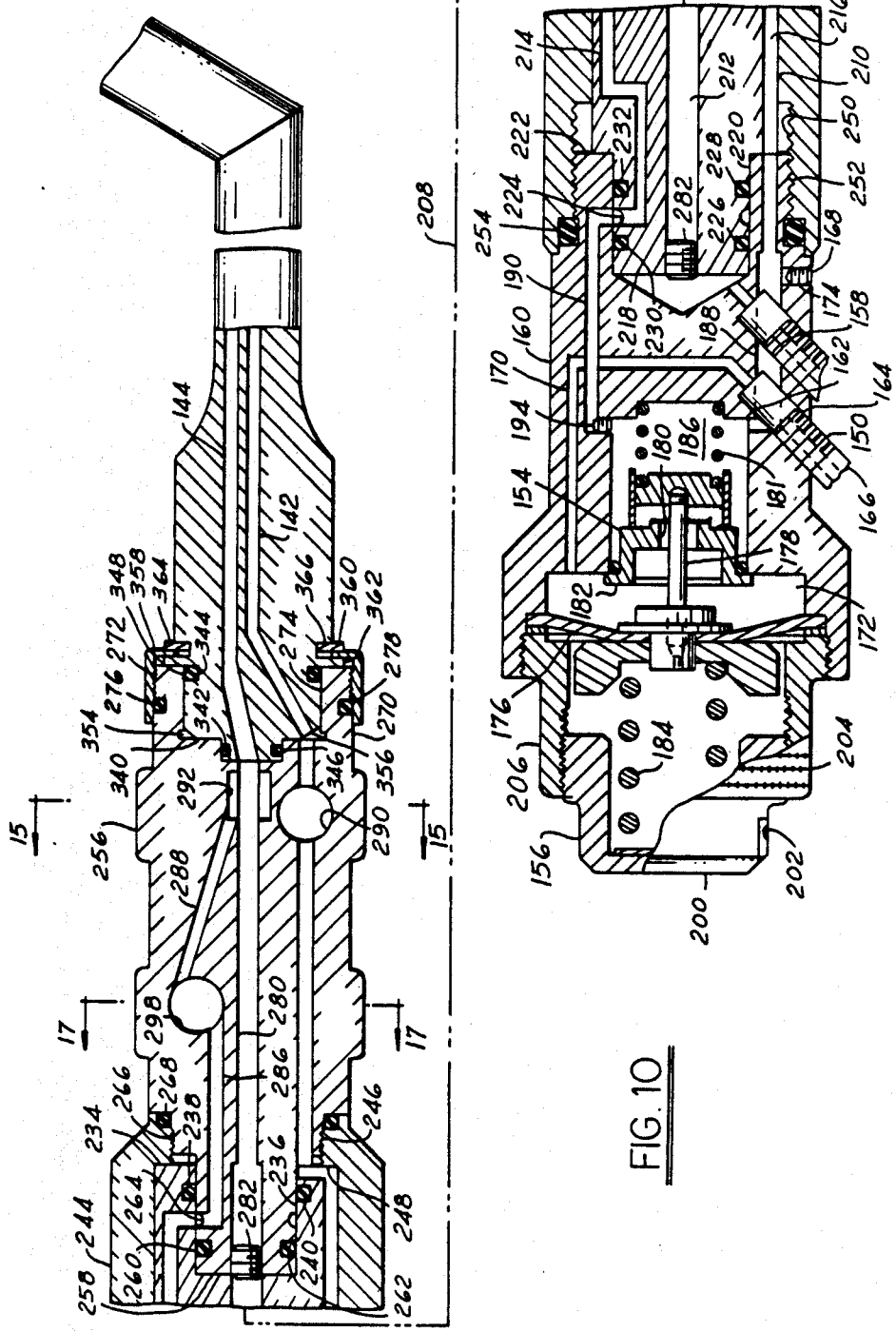
FIG. 10 is an enlarged broken longitudinal section view of a portion of the tissue pneumatic separator shown in FIG. 7.

As shown in FIG. 1, the simplest embodiment of the tissue separator of the invention is a mechanical nudger or tissue separator 10 including a hollow handle 12, a stem 14 secured to the handle 12 by stem retainer 16 and further including tip 18 and tip retainer 20. An end cap 24 is provided on the hollow handle 12 as shown.

The hollow handle 12 is generally cylindrical and has the thumb and forefinger depressions 26 and 28 therein. The end cap 24 is secured to the hollow handle 12 by convenient means such as screw threads 30. Similarly, the stem 14 is secured to the handle 12 by the stem retainer 16 which is provided with a radially extending flange 32 engaging a radially extending flange 34 on the stem 14. The stem retainer 16 is secured to the end of the handle 12 by convenient means such as the screw threads 36 shown in FIG. 2. See, for example, details of FIG. 10 for specific structure providing finger-tight preset friction using O-ring sealing members.

The tip 18 is provided with screw threads 38 on the inner end thereof and is provided with a bulbous outer end 40. Alternatively, the tip 20 may be provided with an interference fit. If the tip and stem are plastic, the interference fit may be followed by an ultrasonic weld. The bulbous other end 40 is utilized to gently nudge tissue to be separated to cause separation thereof. The tip retainer 20 is provided with threaded recesses 42 and 44 in the opposite ends thereof for receiving the threaded end 38 of the tip 18 and the threaded projection 46 on the end of the stem 14.

In use, the tissue separator 12 is held by the handle 12 by a surgeon having his thumb in the depression 26 and his finger in the depression 28 and the tissue to be separated is gently nudged with the bulbous end 40 on the tip 18.

The entire stem 14, tip retainer 20, and tip 18 may be a throw-away item for use in only a single surgical procedure.

Further, as shown best in FIG. 2, the stem 14 may be bent at an angle to facilitate tissue engagement with the bulbous end 40 and better viewing for the surgeon. As shown in FIG. 2, the axis 50 of the tip 18 may make an angle of, for example, 60° with the axis 48 of the stem 14. The particular angle of 60° is, however not critical but has been found to be particularly useful. Also, while the stem 14 is preferably bent to extend upward with the tissue separator 10 in use, it may be bent and/or rotated about its axis in any desired direction.

In this regard, it will be understood that the stem may be of resilient, flexible or maleable material and may be bent as desired. Thus, for example, the stem may be constructed of stainless stell, plastic or aluminum, as desired.

In the modified tissue pneumatic separator 52 shown in FIG. 3, a fluid medium under pressure is connected to the hollow handle 56 through the coupling 58 on end cap 59 and the flexible conduit 60 from a source of fluid medium under predetermined head pressure, not shown. Further, the stem 62, the tip 64 and the tip retainer 66 of the tissue pneumatic separator 52 are provided with axially aligned, axially extending passages 68, 70 and 72, respectively, in communication with the fluid medium from the hollow handle 56.

Thus, in use of the tissue pneumatic separator 52, the fluid medium under pressure, which may for example be nitrogen gas or other fluid non-injurious to the tissue being separated and to its vascular system, is utilized at selected head pressures to separate tissue such as tumor sacs from adjacent healty tissue by blowing the fluid medium through the end of the tip 64 at the tissue at the interface between the tissue to be separated. The tissue separation may also be aided by gently nudging physically with the bulbous end 74 of the tip 64.

In a more sophisticated tissue pneumatic separator, as shown in FIGS. 4 and 5, the tip 76 is floated on a cushion of the fluid medium whereby the possible pressure applied during mechanical nudging with the bulbous tip 78 is controlled in accordance with the pressure of the fluid medium.

As shown in FIG. 4, the end 80 of the modified stem 82 is provided with a threaded extension 84 as before and an axially extending passage 86 is provided extending through the stem 82 in communication with a source of fluid medium under pressure. A recess 88 is also provided in the end 80 of the stem 82.

The tip 76 is generally cylindrical and has an inner end 90 positioned within the recess 88 for axial reciprocation therein, which end 90 has an axially extending recess 92 therein, as shown. The other end 78 of the tip 76 is a bulbous tissue separator as indicated previously. An annular radially extending flange acting as a piston 94 is provided centrally of the tip 76, as shown.

A calibrated radially extending passage 96 extends from the recess 92 in the end 90 of the tip 76 through the outer surface of the tip 76 positioned as shown. A further axially extending passage 98 or calibrated orifice extends through the bulbous outer end 78 of the tip 76. Particularly useful diameters for the passage 98 with fluid medium pressures from 3.5 to 25 p.s.i. have been found to be 0.016, 0.025 and 0.032 inches.

The tip retainer 100 is generally cylindrical and has an internally threaded inner end 102. The outer end 104 is terminated in a radially inwardly extending generally flared, bulbous annulus 106 generally in radial alignment with an annular groove 108 in the tip 76. A plurality of angularly separated, axially and radially extending slots 110 are provided around the inner surface of the tip retainer 100 as shown in FIG. 4 to permit fluid medium under pressure to bypass the annular flange 94 on the tip 76 to cause the tip 76 to float on the fluid medium in use.

Opposing flat surfaces 95 and 97 are provided on tip retainer 100 to facilitate assembly and disassembly of the tip retainer 160 on stem 62.

In use of a tissue pneumatic separator such as that illustrated in FIG. 3 having a floating tip 76 as illustrated in FIG. 4 thereon, the fluid medium passes through the passage 86 through the recess 88 and recess 92 radially outwardly through the passage 96 and through the slots 110 to provide a force, tending to push the tip 76 to the right in FIG. 4, equal to the force due to the pressure acting on the surface of the end 90 of the tip 76 and the pressure on the side 112 of the annular flange or piston annular surface 94.

This force is counteracted by the pressure of the fluid medium on the side 114 of the annular flange or piston 94 and pressure on the bulbous end 78 of the tip 76 due to physical nudging with the tip 76 to separate tissue and/or any back pressure which might be provided on the end 78 of the tip 76 due to the fluid medium under pressure exiting through the calibrated orifice 98 of the tip 76.

The passages 96 and 98 and to a lesser extent the areas of the slots 110 and annulus between the groove 108 and annulus 106 determine the load at which the tip 76 will retract when nudged against tissue due to the cushion of gas existing between the tissue and the bulbous tip or nudged directly via physical contact on the tissue. This is why the tip has been designated a floating tip. That is to say, all these predetermined factors establish the load on the end 78 of the tip 76 which will cause the tip to retract and move to the left in FIG. 4. Typically a nudging load, with a tip jet orifice of 0.031 can be at little as 4 grams under a head pressure of 8 p.s.i.

It will be understood that movement to the right of the tip 76 is limited by the bulbous annulus 106 on the tip retainer 100 while the movement to the left of the tip 76 is limited by the outer end surface 116 of the stem 82.

Further, it will be understood that with the particular floating tip structure illustrated in FIG. 4 that the fluid medium exiting through the calibrated orifice 98 will produce a thin pencil of relatively high pressure fluid medium for separating tissue while an annulus of lesser pressure will be provided between the bulbous end 106 of the tip retaining structure 100 and the annular groove 108 about the stem 76. The lower pressure annulus is particularly useful in continuously clearing the area around the tissue being separated.

The modified floating tip structure illustrated in FIG. 5 is in all respects similar to that shown in FIG. 4 with the single exception that the axial passage 98 has been eliminated from the end 109 of the tip 111. With such structure as that shown in FIG. 5, the tissue separating may be accomplished by mechanical nudging of the tissue to be separated by the bulbous end 109 of the tip 111 which nudging is limited by the floating pressure of the tip 111. Such limiting of the nudging pressure due to the floating tip prevents injury to the tissue being separated.

While the structure of FIG. 3 is intended in its preferred use to be utilized to separate tissue, particularly in conjunction with the floating tips as illustrated in FIGS. 4 and 5, other uses therefor are contemplated. Thus, for example, the structure of FIG. 3 may be utilized by dentists or others for cleaning teeth and between teeth. In such application, as shown in FIG. 6, the flexible conduit 60 may be connected to a source of water under pressure such as a normal hot and cold water mixing faucet 118 directly, if desired, or as shown in FIG. 6 through a water pressure regulator 120 and/or a water pulse forming structure 122. With the structure of FIG. 3 so connected, the water under pressure exiting from the tip 72, or more preferably from the floating tip 76 illustrated in FIG. 4, when directed at the teeth and gums may be utilized to wash away undesirable accumulation of food particles and the like from the teeth and gum area. The floating tip literally rides over the teeth following their contour.

The tissue pneumatic separator 120 illustrated in FIGS. 7-17 is more sophisticated than that shown in FIGS. 3-6. As shown in FIG. 7, the tissue pneumatic separator 120 includes a body assembly 124 having a pressure regulator subassembly 126 and a manifold subassembly 128. A valve unit 130 is provided between the stem 134 and the manifold subassembly 128. The stem 134 is again secured to the valve unit 130 by means of stem retaining structure 136 and a floating tip 138 is connected to the stem 134 by tip retainer 140.

The stem 134, which again may be disposable, is provided with an axially extending passage 142 through which fluid medium is passed to the tip 138 and with a parallel radially displaced passage 144 through which fluid medium is passed towards or withdrawn from around the tip 138, as will be seen subsequently. Also, as particularly shown in FIG. 9, the stem 148 may be straight or the end 144 thereof may be displaced at an angle from the longitudinal axis 146 of the tissue pneumatic separator 120, as before.

The outer hollow cylindrical member 244 of the manifold subassembly 128, as shown best in FIG. 10, includes the inwardly extending threaded flange 246 thereon which provides an abutment 248 on which end 234 of the inner cylinder 210 rests. The other end of the outer cylinder 244 is internally threaded at 250 and mates with the externally threaded end 222 of the body member 160 of the tissue pneumatic separator 120. An annular O-ring seal 254 is provided between the body member 160 and the outer cylindrical member 244 as shown.

For clarity, the straight stem has been numbered 148 in FIG. 9 to distinguish it from the stem 134 having an angularly displaced end 144. All other reference numerals in FIG. 9 are the same as those used in FIG. 7 for the same parts and their functions disclosed therein.

As shown in more detail in FIG. 10, the pressure regulator subassembly 126 of the body assembly 124 includes inlet structure 150 for a fluid medium under pressure, pressure control structure 154, variable indicator structure 156 for the pressure control structure 154, fluid outlet structure 158, and regulator fluid pressure tap 152, all secured to or part of body member 160 which is cylindrical and has the general longitudinal section shape illustrated best in FIG. 10.

Fluid pressure tap 152 which includes threaded opening 174 and plug 168 allows assembly insertion of pressure inspection means or means for visual display of regulated pressure, if so desired, by the operating surgeon. It may also be used by the manufacturer to calibrate the built on pressure regulator 154 and indicator 156 as documented later on.

As shown in FIG. 10, the fluid medium inlet structure 150 includes a recess 162 in the body member 160 having a threaded outer end 164 for receiving a flexible conduit 166 which provides an umbilical cord through which fluid medium such as nitrogen gas under pressure is passed into the tissue pneumatic separator 120. Typical gas pressure from an externally controlled source at inlet structure 150 is 50 p.s.i.

The pressure regulator control structure 154, as shown, includes an annular diaphragm 176 having a needle valve 178 secured thereto for metering the pressurized fluid medium through the opening 180 in the valve member 182. As shown, the position of the needle valve 178 is controlled by the force of bias spring 181 and the adjusting spring 184 which through mechanical connecting structure act on the opposite ends of the needle valve 178.

Thus, in accordance with the axial position of the needle valve 178 in the opening 180, the pressure from the chamber 172 is dropped in a controlled manner into the chamber 186, from whence it is passed into the manifold subassembly 128 through the passage 188 in the body member 160. Typically, regulated pressure levels of 3 p.s.i. to 35 p.s.i. are obtained and used in chamber 186.

The pressure in the chamber 186 may also be passed into the manifold subassembly 128 through the passage 190 in the pressure regulator subassembly 126 if desired in different embodiments of the tissue pneumatic separator 120, as will be seen subsequently. Thus, the plug 194 may be in position in the passage 190 or not depending on the desire for pressurized fluid medium at certain places, and in the floating tip having certain characteristics, as will be seen subsequently.

The variable pressure indicator structure 156 includes the rotary end cap 200 having the indicator dot 202 thereon. The indicator dot 202 functions in conjunction with the graduations 204 marked on the cylindrical member 206 secured to the body member 160 to indicate the exact head pressure which the pressure control structure 154 provides in the chamber 186. Thus, the pressure of, for example, 50 p.s.i. in the chamber 172 may be reduced to 5 p.s.i. or less in the passages 188 and 190 and the value of the pressure is indicated by the graduations 204 and the position of the dot 202 on the rotary end cap 200 and the number of rotations of the end cap 200. As said previously calibration can be performed by using a pressure gauge inserted in the fluid pressure tap 152 threaded opening 174.

Thus, for the first 360° of rotation of end cap 200, the outer graduation scale is utilized in conjunction with the dot 202 to provide a pressure reading within the chamber 186 of up to about 18 p.s.i. For the next 360°, the center graduation scale is utilized in conjunction with the dot 202 to provide an indication of the pressure in the chamber 186, and so on through the number of permitted rotations of the rotatable end cap 202. The pressure within the chamber 186 is thus completely variable in accordance with the angular position of the rotatable cover 200 over several complete revolutions, generally two, thereof.

The manifold subassembly 128 as shown in FIG. 10 extends between the pressure regulator subassembly 126 and the valve unit 130, as shown in FIG. 7. The manifold subsection 128 is broken in FIG. 10 with the connection between the broken parts thereof shown by the construction line 208.

More specifically, the manifold subassembly includes an inner cylinder 210 having an axial passage 212 extending therethrough. Further, cylinder 210 has a passage 214 and a groove 216 imbedded on the outer surface of the inner cylinder and extending longitudinally over substantially the entire length thereof, thus creating a second passage for the fluid medium in conjunction with the outer cylinder 244 considered subsequently.

Fluid medium is passed to the valve unit 130 through the passages 214 and 216, while either a fluid medium at a different pressure or a moisturizing liquid may be passed through the central passage 212, or fluid from tissue being separated may be withdrawn through the passages 212 to be passed out of the tissue pneumatic separator 120 through the outlet structure 158.

As shown in FIG. 10, the reduced diameter end 218 of the inner cylinder 210 of the manifold subassembly 128 is positioned within the recess 220 in the end 222 of the body member 160 of the pressure regulator subassembly 126. An annular groove 224 is provided on the outer surface of the inner cylinder 210 at the end 218 thereof for circumferentially distributing fluid medium from the passage 190 to insure that the fluid medium passes into the passage 214 from the passage 190 regardless of the relative angular position of the inner cylinder 210 and the body member 160. Sealing O-rings 226 and 228 extend annularly around the end 218 of the inner cylinder 210 in grooves 230 and 232 provided on opposite sides of the annular recess 224 as shown in FIG. 10.

The end 234 of the inner cylinder 210 of the manifold subassembly 128 is provided with recess 236 therein having the internal annular groove 238 therearound in which the O-ring seal 240 is positioned as shown in FIG. 10.

The outer hollow cylindrical member 244 of the manifold subassembly 128 as shown best in FIG. 10 includes the inwardly extending threaded flange 246 thereon which provides an abutment 248 on which end 234 of the inner cylinder 210 rests. The other end of the outer cylinder 244 is internally threaded at 250 and mates with the externally threaded end 222 of the body member 160 of the tissue pneumatic separator 120. An annular O-ring seal 254 is provided between the body member 160 and the outer cylindrical member 244 as shown.

Valve unit 130 as illustrated in FIG. 10 includes the valve body member 256 which is generally cylindrical. End 258 of the body member 256 includes a sealing O-ring 260 within an annular groove 262 therearound. End 258 of valve body member 256 is provided with annular groove 264 therearound to insure communication of pressure medium between passage 214 and passage 286. The valve unit body member is secured to the outer cylinder 254 of the manifold structure 128 by means of the threaded end portion 246. An O-ring seal 268 is provided between the valve unit body member 256 and the outer cylinder 244 of the manifold subassembly 128.

The other end 270 of the valve body member 256 is provided with external threads 272 therearound and with a recess 274 therein as shown. An annular groove 276 extends around the outer surface of the end 270 of the valve body member 256 as shown in which the annular sealing ring 278 is positioned.

An axially extending passage 280 is provided in the valve body member 256. In the modification of the tissue pneumatic separator 120 shown in FIG. 10, the passage 280 is provided with a plug or plug function 282 at end 258 of the valve unit body member 256, as shown.

The valve unit body member 256 is further provided with passage 284 extending axially therethrough radially displaced from the passage 280. In addition, passages 286 and 288 are provided in the valve body member 256 extending respectively between annular groove 264 and the valve recess 290 and the annular recess 292 surrounding the passage 280, as shown.

Valves 294 and 296 are provided in valve recesses 290 and 298 between passages 286 and 288 and in passage 284, as shown. The valves are entirely similar and are shown best in FIGS. 15, 16 and 17. The valves 294 and 296 may be constructed of suitable plastic having a desirably low coefficient of friction such as Teflon which is autoclavable, or Delrin which is not autoclavable, but which may be chemically or otherwise sterilized.

As shown, the valve 294 includes a head 300 having a plastic cap 302 thereover with annular grooves 304 therein to prevent slippage of a surgeon's fingers there-from and the valve stem 306 extending from the valve head 300, into the recess 290. The valve stem 306 has the metering annular recess 308 extending therearound as shown best in FIG. 16 and is provided with a plurality of sealing lands 310 between the metering groove 308 and the head 300 as shown in FIG. 16. If necessary, a sealing packing 312 is provided between some of the lands 310.

The end 314 of the valve stem 306 has a recess 316 which is adapted to receive the spring 318 extending between the recess 316 and a similar recess 320 in the cup-shape bottom valve member 322. The spring 318 urges the valve stem 306 out of the recess 298.

The valve stem 306 is maintained in the recess 298 by the pin 324 positioned in the slot 326 in the stem 306. The length of the slot 326 equals the travel of the valve 294. Pin 328 is provided to retain the cup-shape spring retainer 322 in recess 290.

As will be seen from a review of FIGS. 15 and 17, the passages 290 and 298 extend completely through the valve body member 256 and the openings for the pins 324 and 328 are symmetrically positioned in the passage whereby the valves 294 and 296, and in particular the valve 296, may be reversed, that is, placed on the opposite side of the valve body member 256 to permit use of the tissue pneumatic separator by a left-handed operating surgeon.

Thus, in operation of the valve structure 294, when the valve stem 306 is depressed against the bias of the spring 318, the annular metering groove 308 is aligned with the passage 284 to permit fluid medium to flow through the valve unit 130 in the passage 284.

Similarly, when the valve stem 330 is moved to the left in FIG. 17, the metering groove 332 is aligned with the passages 286 and 288 whereby fluid medium is passed from the passage 286 to the passage 288.

As shown best in FIGS. 15 and 17, the passages 284 and the passages 286 and 288 are displaced radially from the central passage 288 and are angularly displaced from each other about the longitudinal axis 146 of the tissue pneumatic separator 120 by 90°. For economy sake, the passages in the body assembly and the metering unit 256 are shown in the same plane in the longitudinal section of FIG. 10 and therefore in the section of FIG. 10 are shown out of position.

As previously considered, the stem 134 of the tissue pneumatic separator 120 may be a disposable stem suitable for a single surgical procedure, after which it may be discarded. Alternatively, of course, the stem 134 may be made of suitable material such as Teflon for placing in an autoclave or other sterilizing atmosphere for repeated re-use, as considered above. Also, as set forth above, the stem 134 may be of any desired length and may be constructed of rigid material such as stainless steel or resilient, flexible or maleable material such as steel, plastic or aluminum.

The end 340 of the stem 134 shaped as shown is positioned in the recess 274 in the valve unit body member 256 with annular sealing rings 342 and 344 in grooves 346 and 348.

As shown, the stem 134 is provided with the radially displaced passage 144 extending therethrough and the axial passage 142. The passage 144 is in communication directly with passage 280 in the valve unit 130, while the passage 142 is in communication with the passage 284 in valve unit 130 through the annular space 354 provided by the beveled surface 356 on the end 340 of the stem 134.

Stem 134 is secured to the valve unit 130 by the stem retaining structure 136. Stem retaining structure 136 includes the annular flanged member 358 having the axial cross section as shown in FIG. 10, and the C-shaped clamp 360. In assembly, the annular member 358 is sleeved over the stem 134 and abuts the annular flange 362 on the stem 134 to secure the stem 134 against the end surface 364 of the valve body 256 on threaded engagement of member 358 with the threads 272 on the valve body member 256. The snap ring 360 is then inserted in the annular groove 366 in the stem 134 to lock the member 358 in place.

The stem retaining structure 136 having the structure shown in FIG. 10 may thus be secured to the valve body member 256 with the annular member 358 finger tight. The stem 134 is rotatable about its axis while a seal between the valve body member 256 and the stem 134 is maintained. The seal between body member 256 and the stem 134 also provides friction, which allows orientation of the angle type tip and insures it will stay put as directed by the operator.

Floating tip 370 is secured on the end of the stem 134 by tip retainer structure 372 as shown best in FIG. 11. The floating tip 370 and tip retainer 372 as shown in FIGS. 11 and 12 are the same as the floating tip 76 and tip retainer 100 shown in FIG. 4 and will not therefore be considered again in detail. It will be noted, however, in conjunction with FIG. 11, that the passage 144 from the stem 134 is in communication with the area behind the annular flange 374 on the tip 370.

Thus, in operation of the tissue pneumatic separator 120 shown in FIGS. 7-12 and FIGS. 15, 16 and 17 as described immediately above, the pressure of the fluid medium tending to push the floating tip to the right in FIG. 11 is or may be determined, not only by the pressure in the passage 142 in stem 134, that is, the pressure controlled by the valve 294, but is also controlled in accordance with the pressure in the passage 144 under control of the valve 296.

Pressure in the passage 142 will be the pressure from chamber 186. Pressure in passage 144 will, however, vary depending on which of plugs 194 and 282 are in place and what, if any, fluid medium is connected to outlet structure 158. Thus, with both plugs 194 and 282 in place, no fluid medium will be present in passage 144. Therefore, only calibrated orifice 378 is in use and cleaning action is obtained through gas or liquid fluid escaping through passage 375 as considered in conjunction with floating tip 76 of FIG. 4.

With only plug 282 in place, the pressure in passage 144 will be that in chamber 186 also. With only plug 194 in place, the pressure in passage 144 will be that connected into outlet structure 158.

In any event, there is provided in accordance with the fluid medium pressure operating on the floating tip 370, a pressure tending to move the floating tip 370 to the right in FIG. 11, as before. The force available to effect tissue separation with the bulbous end 376 of the tip 370 is then the residual force necessary to move the tip 370 to the left in FIG. 11 in opposition to the fluid pressure forces acting on the tip 370 from the passages 142 and 144.

Again, a thin pencil of fluid medium will pass through the passage 378 in the tip 370 to impinge upon and tend to force separation of tissue immediately in front of the bulbous tip 376, as before. Also, as before, a fluid medium pressure will be exerted around the outside of the tip 370 to clear away the area about the tissue being separated if one of plugs 194 and 282 are removed and pressure is then present in passage 144.

With such operation, it will be noted that the operating surgeon is in complete control of the fluid medium pressures in passages 142 and 144 due to the inclusion of the valves 294 and 296 in the tissue pneumatic separator 120. In this respect, the tissue pneumatic separator 120 is considerably more sophisticated than the tissue pneumatic separator 52 illustrated in FIG. 3, if so required by the surgical procedure.

In the modified tissue pneumatic separator structure 380, as shown best in FIG. 18, the valve unit 382 is modified by replacing the plug 282 in the tissue pneumatic separator 120 with a plug 384 having an axially extending passage 386 therethrough positioned in the axially extending threaded recess 388 in the valve body member 390.

Further, the valve unit 382 includes an aspirating pipe 392 positioned in the axial passage 394 and held therein by the threaded end 396 thereof in the recess 388. A check valve 398 is urged into closing relation to the passage 386 through plug 384 by the bias spring 400, as shown best in FIG. 18, to prevent fluid under pressure in passage 412 from passing upstream.

With such structure, a source of moisturizing fluid such as water is connected through umbilical cord 402 in outlet structure 404 whereby water is placed in passage 406 of the manifold subassembly 408.

With the modified tissue pneumatic structure 380 shown in FIG. 18, with the proper differential between the spring pressure on the check valve 398 and the water pressure in the passage 406, the valve 398 will be caused to open when a sufficient vacuum is provided at the end of the aspirating pipe 392 due to a venturi effect produced by the fluid medium from the passage 410 passing through the passage 410 and into the passage 412.

The moisture from the aspirating pipe 392 is thus mixed with the fluid medium such as nitrogen gas in the passage 412 and passed around the floating tip 370. Thus, with the modified tissue pneumatic separator 380 shown in FIG. 18, the tissue being separated may be moisturized under separate thumb control of valve 296 while it is being separated under forefinger control of the other valve 294.

The further modified tissue pneumatic separator 420 shown in FIG. 19 includes an outlet connection 422 to the umbilical cord 424 through which blood or other fluids about tissue being separated may be evacuated from the area of the tissue being separated through the tissue pneumatic separator modification 420.

Thus, the umbilical cord 424 is connected directly to the passage 426 in the manifold subassembly 428 with the plug 194 removed and the passage 434 returned by a passage portion 436 whereby the fluid medium such as nitrogen gas or the like flows through the passage 430 to the left as shown in FIG. 19 (reverse venturi effect).

The flow of the nitrogen gas through the passage 430 to the left in FIG. 19 creates a vacuum or suction about the tip 438 as shown in FIG. 13, whereby blood and other debris from separating tissue may be sucked through passage 440 in the stem 442 to be discharged ultimately from the umbilical cord 424.

The joining ends of the passages 434 and 436 in the valve unit 432 are plugged by means of plug 444 for construction purposes.

As shown best in FIG. 14, the floating tip 438 is somewhat modified as is the inside configuration of tip retainer 446. Thus, the annular flange 473 of the tip 370 is reduced to flange portions such as portions 448 shown in FIG. 14 necessary to guide the tip 438 in its reciprocal movement in the tip retainer 446. This provides enlarged areas 450 through which debris from separating tissue may be drawn into the tissue pneumatic separator 420. The enlarged openings 450 do away with the need for the slots 452 as shown in FIGS. 11 and 12.

In all other respects, the structure of and the method of operation of the tissue pneumatic separator 380 and 420 are identical with the structure and operation of the tissue pneumatic separator 120.

While different embodiments and modifications of the invention have been considered in detail above, it will be understood that other embodiments and modifications thereof are contemplated by the inventor.

Thus, for example, the structure of the invention may be used as an external ear cleaning device for wax removal with the nitrogen gas being replaced by a warm oil. In such applications the floating tip would be less likely to injure an eardrum or other sensitive portions of the external ear than would the usual cotton swabs and the like utilized currently in cleaning ear passages.

Further, the device of the invention can be used as an adjunct to other surgical equipment in a plurality of different applications such as in performing an endoscopy, a bronchoscopy, a proctoscopy, or a sigmoidoscopy. Many such procedures would, of course, require the stem to be elongated and the device of the invention included in such procedures would include any one of viewing or illuminating structure therein.

It is the intention to include all embodiments and modifications of the invention, which are all part of a new surgical process defined by the appended claims within the scope of the invention.

What is claimed is:

1. A tissue separator comprising a handle, a stem having a longitudinal axis secured to the handle, tip means retained on one end of the stem including blunt tissue separating means at one end thereof for mechanically separating tissue along natural cleavage planes without cutting of the tissue on nudging of the tissue with the tissue separating means, wherein the handle, stem and tip are hollow to provide for the flow of a fluid medium into the hollow handle, and wherein the tip is not fixed relative to the stem but is a floating tip and means for moving the floating tip axially relative to the stem in accordance with the pressure of the fluid medium acting in balance on the tip.

2. Structure as set forth in claim 1 wherein the floating tip is secured to the stem by means of a tip retainer, the tip retainer is generally cylindrical and includes angularly spaced apart radially extending slots on the inner surface thereof, wherein the stem has a recess in the one end thereof to which the tip retainer is secured and wherein the floating tip comprises a generally cylindrical member having the tissue separating means at one end thereof, a radially extending annular piston flange located centrally thereof, a recess extending axially into the other end thereof, and an opening extending radially of the tip on the one end side of the annular flange through the tip into communication with the recess in the other end of the tip whereby with the other end of the tip positioned in the recess in the one end of the stem the tip is caused to float in the tip retainer.

3. Structure as set forth in claim 2 wherein the one end of the tip is bulbous and solid.

4. Structure as set forth in claim 2 and further including an axial passage acting as a calibrating orifice in the one end of the tip extending between the bottom of the recess in the other end of the tip through the one bulbous end of the tip.

5. Structure as set forth in claim 1 wherein the fluid medium is nitrogen gas.

6. Structure as set forth in claim 1, wherein the fluid medium is water and further including means for connecting the means connecting the fluid medium to the hollow handle to a source of water under pressure.

7. Structure as set forth in claim 6 wherein the means for connecting the handle to a source of water under pressure includes a pressure regulator.

8. Structure as set forth in claim 6 wherein the means for connecting the handle to a source of water under pressure includes a pulse former for providing the water to the handle in discrete pulses.

9. Structure as set forth in claim 1 wherein the means for moving the floating tip in accordance with the pressure of the fluid medium acting in partial balance on the tip's effective piston area includes means for moving the tip axially outwardly relative to the stem bore in accordance with said pressure.

10. A tissue pneumatic separator comprising a body assembly including a rear pressure regulator subassembly and a front manifold subassembly, a valve unit connected to the manifold for metering regulated fluid medium to and from the manifold subassembly, a stem, stem retaining structure for securing the stem to the valve unit, a floating tip, means for floating said tip on said fluid medium, a tip retainer for retaining the tip on the stem, and means for securing the tissue pneumatic separator to a source of fluid medium under pressure.

11. Structure as set forth in claim 10, wherein the pressure regulator subassembly includes means for variably controlling the fluid medium pressure over a relatively wide pressure range.

12. Structure as set forth in claim 11 wherein the means for controlling the fluid medium pressure includes pressure control structure operable on rotation of a control knob, a rotary control knob on the pressure regualtor subassembly for controlling the pressure control structure and variable indicia of the pressure of the fluid medium in the pressure regulator subassembly adjacent the control knob for indicating the pressure of the fluid medium in the pressure regulator subassembly in accordance with particular settings of the control knob over more than 360° of rotation of the control knob.

13. Structure as set forth in claim 10 wherein the pressure regulator subassembly includes inlet means for passing the fluid medium into the pressure regulator subassembly and further means for passing the fluid medium into or other fluids out of the tissue pneumatic separator.

14. Structure as set forth in claim 10 wherein the manifold subassembly includes an inner cylinder having at least one passage therethrough extending axially thereof and at least one longitudinally extending channel on the outer surface thereof and an outer hollow cylinder sleeved over the inner cylinder.

15. Structure as set forth in claim 10, wherein the valve unit includes longitudinally extending passages therethrough and valve structure extending transversely of the valve unit and intersecting at least one of the passages therethrough operable to meter the flow of fluid medium through the valve unit.

16. Structure as set forth in claim 15, wherein the valve unit is cylindrical and includes a central longitudinally extending passage therethrough, one end of which may be closed and a second longitudinally extending passage in said valve unit, one end of which terminates at one end in the first longitudinally extending passage through the valve unit and a valve extending through the second passage for metering fluid medium through the valve unit.

17. Structure as set forth in claim 16 and further including an elongated moisture aspirating pipe in the first elongated passage and a check valve in the aspirating tube whereby moisture is drawn into the central passage through the check valve on vacuum of a predetermined negative pressure being present in the elongated passage.

18. Structure as set forth in claim 16, and further including an elongated moisture aspirating pipe in the first elongated passage and a check valve in the aspirating tube whereby moisture is drawn into the central passage through the check valve on vacuum of a predetermined negative pressure being present in the elongated passage.

19. Structure as set forth in claim 16 wherein the second passage is in communication with the central passage in a direction to produce a flow of fluid medium through the control passage in a direction opposite that of the tip of the tissue pneumatic separator, whereby a suction will be provided at the tip.

20. Structure as set forth in claim 10, wherein the stem is in an elongated member having a pair of longitudinally extending passages therein, one of which is in communication axially with a passage through the valve unit and the other of which is in communication with a beveled surface on the end of the stem to receive fluid medium from the valve unit proceeding annularly about the beveled surface, whereby the stem may be connected in any angular position with respect to the valve unit.

21. Structure as set forth in claim 10, wherein the stem is a throw-away unit adapted to be used once and then discarded.

22. Structure as set forth in claim 10, wherein the stem is provided with a radially extending flange about one end thereof and an annular groove immediately adjacent to the flange and between the flange and the other end of the stem and the stem retaining structure is an annular member having an inwardly extending annular flange thereabout adapted to slip over the stem with the annular flange on the annular member in engagement with the annular flange on the stem and a snap ring member positioned in the annular groove in the stem securing the annular member in position on the stem aganist axial movement relative thereto while permitting relative rotation between the annular member and stem.

23. Structure as set forth in claim 22 and further including a sealing ring positioned between the valve unit and the stem retaining structure of a size to provide frictional resistance to relative rotary motion therebetween.

24. Structure as set forth in claim 10, wherein the floating tip is positioned within the tip retainer and in one end of the stem.

25. Structure as set forth in claim 24 wherein the stem is provided with a central axial passage therethrough terminating in a recess in one end thereof and is provided with a second radially outward annular passage extending therethrough, one end of the floating tip is positioned within the recess in the one end of the stem and includes an axially extending recess therein, said floating tip further including a centrally positioned radially outwardly extending annular piston flange, a bulbous other outer end and a passage extending radially through the floating tip between the annular flange and the bulbous outer end in communication with the recess in the one end of the floating tip, said tip retaining member being generally cylindrical and secured to the end of the stem and having annularly spaced apart longitudinally extending slots in the inner surfaces thereof for passing fluid around the radially extending piston flange on the floating tip in communication with the radially outer opening through the stem.

26. Structure as set forth in claim 24 wherein the stem has an axially extending passage therethrough and a parallel, radially outer, axially extending passage therethrough and a recess in one end thereof in engagement with the axially extending passage, the floating tip has one end having an axially extending recess therein within the recess in the one end of the stem and radially extending guide fins, and a radially extending passage adjacent the guide fins between the guide fins and the other end of the floating tip in communication with the recess in the one end of the tip and wherein the floating tip retaining member is an annular member secured to the one end of the stem and having an internal cylindrical surface in engagement with the outer tips of the guide fins of the floating tip.

27. Structure as set forth in claim 24 wherein the outer end of the tip is provided with a passage acting as a calibrated orifice extending axially completely therethrough to engage the recess in the one end of the tip.

28. Structure as set forth in claim 24 wherein the outer end of the tip is solid.

29. Disposable structure for a tissue pneumatic separator comprising an elongated stem, a stem retaining member for securing the stem to the tissue penumatic separator and a tip on the stem for separating tissue having a piston portion and a guiding shank, said stem and tip having an opening therethrough through which a fluid medium may be passed to separate tissue and means operable between the stem and tip for floating the tip on the fluid medium passing peripherally around the tip piston portion and its guiding shank.

30. Structure as set forth in claim 29 wherein the floating tip includes a solid outer end.

31. Structure as set forth in claim 29 wherein the floating tip includes a calibrated passage extending axially completely therethrough.

* * * * *